United States Patent [19]

Corliss, Sr., deceased et al.

[11] Patent Number: Plant 5,988

[45] Date of Patent: May 19, 1987

[54] EUONYMUS PLANT—CORPREME VARIETY

[75] Inventors: Clifford D. Corliss, Sr., deceased, late of Ipswich; by Clifford D. Corliss, Jr., executor, South Hamilton, both of Mass.

[73] Assignee: The Conard-Pyle Company, West Grove, Pa.

[21] Appl. No.: 747,435

[22] Filed: Jun. 21, 1985

[51] Int. Cl.[4] ..... A01H 5/00

[52] U.S. Cl. ..... Plt./63

[58] Field of Search ..... Plt./63

*Primary Examiner*—Robert E. Bagwill

*Attorney, Agent, or Firm*—Burns, Doane, Swecker & Mathis

[57] ABSTRACT

A new and distinct variety of *Euonymus fortunei* which originated as a branch sport of the Corlutz variety of *Euonymus fortunei* (U.S. Plant Pat. No. 4,795) is provided. The new variety possesses foliage which exhibits a coloration substantially identical to that of the parent, but differs from the parent in several important respects, including a substantially larger leaf size. In addition, the new variety has significantly longer internodes than the parent, and exhibits a more open growth pattern than the parent.

2 Drawing Figures

SUMMARY OF THE INVENTION

The new variety was discovered and selected by Clifford D. Corliss, Sr., (now deceased) of Ipswich, Mass. The variety was discovered by him as a branch sport on a plant of the Corlutz variety of *Euonymus fortunei* (U.S. Plant Pat. No. 4,795) being grown under his direction at the nursery of Corliss Bros., Inc., at Ipswich, Mass. The sporting branch exhibited a leaf size and growth characteristics which differed significantly from those of the parent, while maintaining substantially the same basic leaf coloration as the parent. This branch was preserved in order to further observe the new characteristics and to confirm that it differs from previously reported varieties of *Euonymus fortunei.*

The following combination of characteristics was found to be exhibited by the new variety:

(a) a substantially larger leaf size than both the parent and other known varieties of *Euonymus fortunei,*
(b) a leaf coloration which is dark green with light to medium yellow margins and which is substantially the same as that of the parent,
(c) the propensity to exhibit no substantial leaf coloration change during the winter,
(d) a leaf internode length which is on average approximately twice as long as that of the parent,
(e) a plant growth habit that is more open than that of the parent,
(f) an annual growth rate which is less than that of the parent as a young plant, but which is approximately equal to that of the parent as the plant reaches approximately four to five years of age,
(g) the ability to thrive under a wide range of climatic conditions, and
(h) the ability to be sheared within prescribed limits or shaped to a specific form.

Plants of the new variety two years following propagation when grown in a nursery commonly assume a height of approximately 40 to 45 cm. and a width of approximately 30 to 45 cm. Such young plants commonly exhibit a greater height than width. Plants of the new variety which are approximately 5 to 6 years of age when growing in the landscape commonly assume a height of approximately 60 cm. and a width of approximately 75 cm. Accordingly, the fully mature plants commonly exhibit a greater width than height.

Asexual reproduction of the new variety by cuttings has been accomplished at Ipswich, Mass., and at West Grove, Pa., over a period of at least ten years and has demonstrated that the unique combination of characteristics has been established and is transmitted to successive generations.

The new variety has been named the Corpreme variety, and is being marketed by The Conard-Pyle Company of West Grove, Pa., under Emerald Delight trademark.

BRIEF DESCRIPTION OF THE PHOTOGRAPHS

The accompany photographs show typical specimens of the variety in color as true as is reasonably possible to make the same in color illustrations of this character. The photographs were made in late spring of a representative plant and plant parts thereof growing in the landscape at West Grove, Pa. The estimated age of the plant shown is at least six years.

FIG. 1 illustrates the appearance of a pair of representative plants of the new variety while growing side-by-side, and FIG. 2 illustrates representative branches and plant parts of the new variety.

DETAILED DESCRIPTION

Figure 1:
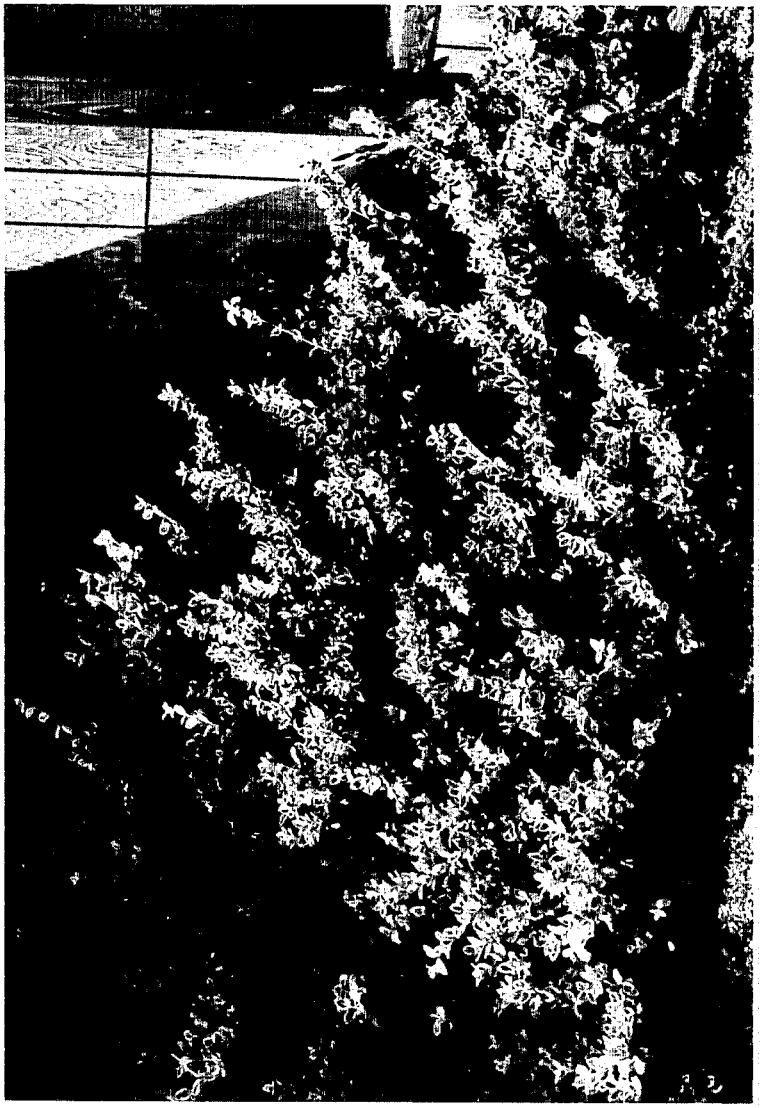
Figure 2:
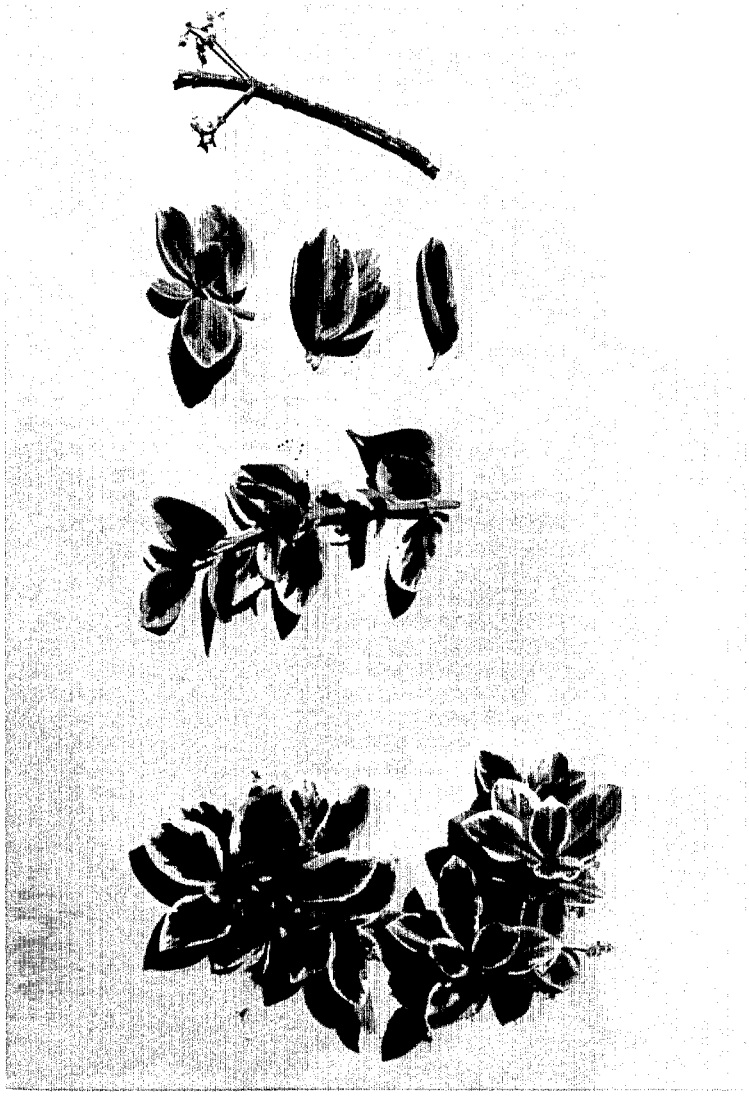

The following is a detailed description of the new variety, with color terminology in accordance with The R.H.S. Colour Chart of The Royal Horticultural Society, London, England. The description was made in early spring from specimens of at least six years of age growing in a landscape situation at West Grove, Pa.

Growth habit: More open than that of the parent. The substantially longer internode length than the parent gives the overall plant a much less dense appearance than the parent. The internode length commonly is approximately twice that of the parent when mature plants are compared.

Foliage:

*Type.*—Broadleaf evergreen, petioled, opposite.

*Shape.*—Slightly variable in shape. Mostly ovate with some eliptic. Base obtuse. Margins are slightly serrate.

*Petioles.*—Approximately 5 to 9 mm. in length.

*Size.*—Somewhat variable as other varieties of *Euonymus fortunei.* However, the leaf size is larger than previously known varieties. Fully expanded leaves commonly range in length from approximately 2.6 to 4.6 cm. (e.g., approximately 3.8 cm. on average), and in width from approximately 1.7 to 3.3 cm. (e.g., 2.6 cm. on average).

*Color-upper surface.*—Immature leaves, Green Group 143A edged with a margin of Yellow-Green Group 151A to 151C, and mature leaves, Green Group 137A to 137B, with a margin of Yellow Group 8B or Yellow Group 13B.

*Color-under surface.*—Duller with less color differentiation than upper surface, commonly Green Group 137C with a margin of Yellow-Green Group 154A.

Flowers: Somewhat more prevalent than on parent, appearing early in June at West Grove, Pa.

Hardiness: Believed to be slightly less hardy than the parent with virtually no damage appearing after exposure to temperatures of −14° F.

I claim:

1. A new and distinct variety *Euonymus fortunei* which is a branch sport of the Corlutz variety, substantially as herein shown and described, characterized particularly as to novelty by the unique combination of:

(a) a substantially larger leaf size than both the parent and other known varieties of *Euonymus fortunei,*

(b) a leaf coloration which is dark green with light to medium yellow margins and which is substantially the same as that of the parent, (c) the propensity to exhibit no substantial leaf coloration change during the winter, (d) a leaf internode length which is on average approximately twice as long as that of the parent, (e) a plant growth habit that is more open than that of the parent, (f) an annual growth rate which is less than that of the parent as a young plant, but which is approximately equal to that of the parent as the plant reaches approximately four to five years of age, (g) the ability to thrive under a wide range of climatic conditions, and (h) the ability to be sheared within prescribed limits or shaped to a specific form.

* * * * *